United States Patent
Rani

[11] Patent Number: 5,764,539
[45] Date of Patent: Jun. 9, 1998

[54] NON-INVASIVE SYSTEM AND METHOD FOR A FLUID FLOW MONITORING SYSTEM

[75] Inventor: Robert G. Rani, Roseville, Minn.

[73] Assignee: Novartis Nutrition AG, Berne, Switzerland

[21] Appl. No.: 184,884

[22] Filed: Jan. 21, 1994

[51] Int. Cl.$^6$ .................................................. G01K 7/00
[52] U.S. Cl. .................... 364/557; 364/509; 364/510; 364/550; 364/551.01; 73/204.11; 73/204.14; 73/204.17; 73/204.19
[58] Field of Search .................. 364/524, 413.01, 364/557, 556, 510, 509, 571.01, 571.03, 550, 551.01; 73/195, 196, 202, 202.5, 204.11–204.19, 204.21–204.24, 861, 861.01–861.03, 861.95, 861.17, 861.19, 861.24, 861.39, 861.44, 861.51, 861.66–861.68, 1.01, 1.02, 1.16, 1.34, 1.73, 1.83; 210/737, 739, 742, 85–90, 104, 744, 97, 98, 103; 128/672, 713, 736, 692, 633, DIG. 12, DIG. 13; 374/107, 112, 116, 118, 128, 132, 133, 135, 137, 141, 142, 148, 170; 604/128, 131, 151, 153, 8, 9, 65–67

[56] References Cited

U.S. PATENT DOCUMENTS

| | | | |
|---|---|---|---|
| 3,891,391 | 6/1975 | Boone | 73/204.18 |
| 4,384,578 | 5/1983 | Winkler | 604/114 |
| 4,388,003 | 6/1983 | Feller | 73/861.03 |
| 4,464,932 | 8/1984 | Ewing et al. | 73/204.15 |
| 4,476,877 | 10/1984 | Barker | 128/736 |
| 4,566,320 | 1/1986 | Bohrer | 73/204.16 |
| 4,770,037 | 9/1988 | Noir et al. | 73/204.12 |
| 4,912,974 | 4/1990 | Inada et al. | 73/204.25 |
| 4,913,703 | 4/1990 | Pasqualucci et al. | 604/153 |
| 4,916,948 | 4/1990 | Inada et al. | 73/202.5 |
| 4,938,079 | 7/1990 | Goldberg | 73/204.23 |
| 4,969,357 | 11/1990 | Mickler | 73/204.11 |
| 5,056,047 | 10/1991 | Sondergeld | 364/510 |
| 5,142,907 | 9/1992 | Hinkle | 73/204.12 |
| 5,174,299 | 12/1992 | Nelson | 73/202.5 |

*Primary Examiner*—Emanuel Todd Voeltz
*Assistant Examiner*—Hal D. Wachsman
*Attorney, Agent, or Firm*—Gabriel Lopez

[57] ABSTRACT

A non-invasive system and method is provided for a fluid delivery system of the type including a fluid delivery pump delivering fluid in pulses through a fluid delivery tube. The non-invasive monitoring system and method includes a sensor which is brought into engagement with an outer surface of the fluid delivery tube. The sensor is adapted for being calibrated at an initial temperature and is responsive to the fluid when passing through the fluid delivery tube. In particular, the present system and method is adapted to monitor the sensor and receives data corresponding to the changes in the initial temperature of the sensor as influenced by the temperature of the fluid when passing through the fluid delivery tube. The non-invasive monitoring system and method is further adapted to process the data from the sensor indicative of both the initial and changed temperatures for determining the status of the fluid in the fluid delivery tube. A display can also be provided for notifying the user of the device of the status of the fluid in the fluid delivery tube.

20 Claims, 2 Drawing Sheets

NON-INVASIVE SYSTEM AND METHOD FOR A FLUID FLOW MONITORING SYSTEM

BACKGROUND OF THE INVENTION

1. Field of the Invention

The present invention relates generally to fluid flow monitoring systems and more particularly to a non-invasive monitoring system and method for a fluid flow system.

2. Description of the Prior Art

There are many different varieties of systems known in the art which are adapted to monitor the fluid flow through a particular system. Such devices employ many various techniques to accomplish such operation. One type is generally accomplished by monitoring the temperature of the fluid being measured. A disadvantage of such prior art systems is that operation is dependent on the property of the fluid being delivered through the system. As a result, such systems have application over a limited range with other types of devices. Generally, such systems employ a flow sensor which is adapted to monitor the temperature of the fluid being measured when delivered through the fluid delivery system.

It has been found that such prior art systems have numerous other limitations which severely inhibit their usefulness in many applications. For example, a problem with many of the prior art devices is that the flow sensor for operation is brought into direct contact with the fluid being delivered through the delivery system. However, in many instances, it is desirable to maintain the integrity of the fluid from contact outside of the system. For example, with fluid delivery systems which are utilized for medical procedures, it is essential that the purity of the fluid be maintained throughout the entire system.

A few devices have been developed in order to isolate the monitoring sensor from the flow of fluid through the delivery system. However, such devices employ complex interfacing arrangements between the sensor and the delivery system which provide a very time consuming and costly procedure for application in a respective fluid delivery system.

Because of these and other difficulties associated with fluid monitoring techniques presently employed, there now exists a need for a simple and economical means for the non-invasive monitoring of fluid flow in a fluid delivery system without the disadvantages of the current monitoring techniques.

SUMMARY OF THE INVENTION

The present invention provides a non-invasive monitoring system and method which is adapted for a fluid delivery system of the type including a fluid delivery pump delivering fluid having a particular fluid temperature in pulses through a fluid delivery tube. For this purpose, the non-invasive monitoring system and method of the present invention includes a sensor means which is adapted for engaging an outer surface of the fluid delivery tube. The sensor means is capable of being calibrated at an initial temperature, with the initial temperature being different from the temperature of the fluid. The sensor means is also adapted to be responsive to the fluid when passing through the delivery tube for changing the initial temperature thereof. The sensor means returns to its initial temperature when the flow of fluid is not being passed through the fluid delivery tube. The sensor means also generates data corresponding with the initial and changed temperatures. For this purpose, means for monitoring the data from the sensor means is provided for detecting the changes in the initial temperature as influenced by the temperature of the fluid when passing through the fluid delivery tube. Means for processing the data from the sensor means is also provided for determining the status of the fluid in the fluid delivery tube.

In accordance with the present invention, an object is to provide a monitoring system and method for a fluid delivery system of the type including a fluid delivery pump delivering fluid in pulses through a fluid delivery tube.

It is another object of the present invention to provide a monitoring system and method for a fluid delivery system that incorporates a non-invasive process wherein the fluid being delivered is not brought into direct contact with the monitoring apparatus.

It is another object of the present invention to provide a non-invasive monitoring system and method for a fluid delivery system wherein a simple interface between the monitoring apparatus and the fluid delivery system is provided.

It is a further object of the present invention to provide a non-invasive monitoring system and method for a fluid delivery system which is inexpensive to construct and sufficiently simple in design and operation.

These and other objects of the present invention will become more readily apparent when taken into consideration with the following description and the attached drawings.

DETAILED DESCRIPTION OF THE PREFERRED EMBODIMENTS

Figure 1:
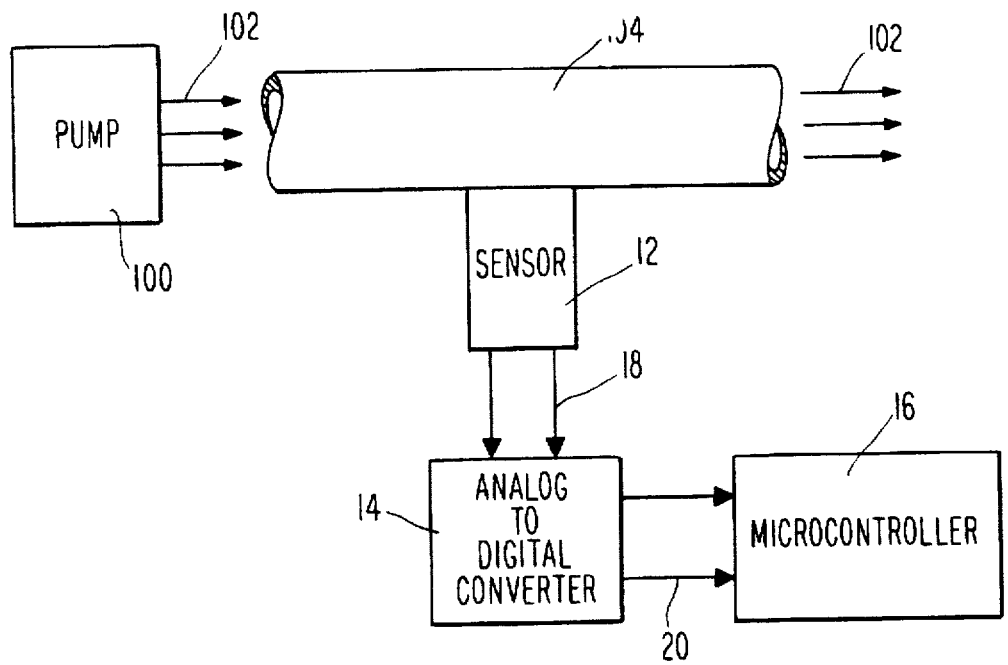
FIG. 1 is a partly schematic and partly block diagram representation of the non-invasive monitoring system and method in accordance with a first embodiment of the present invention.

Referring now to the drawings in detail, wherein like reference numerals indicate like elements throughout the several views, there is shown in FIG. 1 a partly schematic and partly block diagram representation of the non-invasive monitoring system and method in accordance with a first embodiment of the present invention. As indicated earlier, the non-invasive monitoring system and method of the present invention is adapted to be used with a variety of different fluid delivery systems capable of delivering fluid in pulses by operation of a pump through a delivery tube, such as a peristaltic delivery system or a continuous fluid delivery system adapted for start/stop operation, as examples. In particular, in FIG. 1 is shown a pump 100 which is adapted to deliver a fluid in pulses indicated by the arrows 102 through a fluid delivery tube 104 shown in section. The pump 100 is adapted to regulate the flow of the fluid 102 through the delivery tube 104. In operation, the non-invasive monitoring system and method according to the present invention is adapted to monitor the status of the fluid 102 in the delivery tube 104 as will be described in detail below.

The non-invasive monitoring system and method as illustrated in the present embodiment includes a sensor 12, an analog to digital convertor 14 and a microcontroller 16. The sensor 12 can comprise any suitable type of standard temperature sensor which is capable of both being initially calibrated at a particular temperature prior to operation and measuring the temperature of the sensor during operation, for example a self heated temperature sensor, such as a NTC thermistor can be used for this purpose. The sensor 12 as shown is connected via lines 18 to the analog to digital convertor 14. The analog to digital convertor 14 in turn is connected via lines 20 to the microcontroller 16 which comprises a standard microprocessor or similar device.

In operation, the sensor 12 is brought into contact with the outer surface of the fluid delivery tube 104. The sensor 12 in this position is adapted to detect the status of the fluid 102 when passing through the fluid delivery tube 104 adjacent the sensor 12. In particular, the temperature of the sensor 12 is responsive to the temperature of the fluid 102 when passing through the fluid delivery tube 104. To accomplish this operation, the sensor 12 is initially calibrated at a temperature different from the temperature of the fluid 102. In this embodiment, the calibrated temperature is required to be different from the temperature of the fluid 102, however it is not required that the sensor 12 be calibrated at a specific temperature value. Preferably, the initial temperature of the sensor 12 is calibrated at approximately 10° to 20° above ambient temperature of the fluid 102, however other values can also be utilized for the same purpose, for example, the calibrated temperature can be set below ambient temperature of the fluid 102 where desired During operation, the initial temperature of the sensor 12 is altered by the fluid 102 when passing through the delivery tube 104 adjacent to the sensor 12. Specifically, the initial temperature of the sensor 12 is either decreased or elevated, depending on its calibrated temperature, when the fluid is being passed through the delivery tube. As the fluid flow 102 is terminated through the fluid delivery tube 104, the temperature of the sensor 12 will return to its initial calibrated temperature. When no fluid 102 is being passed through the delivery tube 104, the temperature of the sensor 12 will maintain an equilibrium temperature corresponding to the calibrated temperature and any other external temperature influence, such as resulting from the fluid delivery tube 104.

The temperature of the fluid 102 as detected by the sensor 12 is monitored by the system as will be described below. The data associated with the temperature of the sensor 12 is in the form of analog signals which are passed via the lines 18 through the analog to digital convertor 14 for transformation to digital signals for analysis by the system. These digital signals are past via lines 20 to the microcontroller 16 for this purpose. The microcontroller 16 operates to monitor the temperature of the sensor 12 to detect any changes in the initial temperature as influenced by the temperature of the fluid 102. The microcontroller 16 processes the digital signals against preprogrammed information to determine the status of the fluid 102 in the fluid delivery tube 104. For example, the microcontroller can be programmed to compare the digital signals against known digital patterns to determine the status of the fluid 102. In accordance with the present embodiment, the microcontroller 16 is adapted to detect either a steady data signal indicative of a steady temperature pattern, or an oscillating data signal indicative of a changing temperature pattern. The steady data signal is produced by the sensor 12 whenever the fluid 102 is contained within, although not moving through, the fluid delivery tube 104. A steady data signal is also produced in instances when the fluid delivery tube 104 is empty or when no fluid 102 is in the fluid delivery tube 104. An oscillating data signal is provided from the sensor 12 when the fluid 102 is being passed in pulses through the fluid delivery tube 104.

Figure 2:
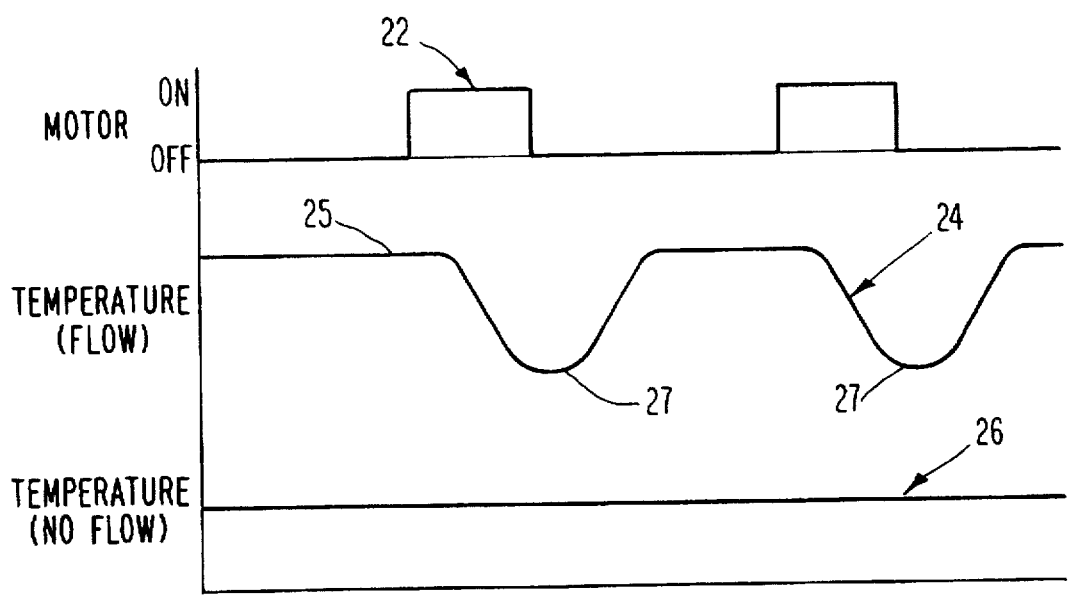
FIG. 2 shows three diagrammatic representations useful to explain the system and method in accordance with FIG. 1.

For example, a set of signals are illustrated in FIG. 2 for better illustration of the above-described procedure. The first signal 22 illustrates the status of the pump 100 during delivery of the fluid 102. For reason of example, the pump 100 is shown here as being adapted to deliver repetitive short bursts of the fluid 102 with a pause in between each fluid burst. In particular, the peaks of the signal 22 illustrate when the pump 100 is in its "on" state, while the off status of the pump 100 is indicated by the level of signal 102 on the line designated by "off". However, it should be understood that the pump 100 can be adapted to deliver the fluid 102 at any particular rate and in any particular sequence depending on the setting of the pump or of the particular type of pump employed. The second signal 24 is illustrative of the oscillating data signal provided from the sensor 12 as the pump 100 is delivering the fluid 102 in pulses through the delivery tube 104. For example, the change in the signal 24 from the upper peak 25 to the lower peak 27 corresponds to the effect of the temperature of the fluid 102 on the temperature of the sensor 12. In this example, the initial temperature of the sensor 12 is elevated above the temperature of the fluid 102. In particular, when the fluid 102 is not being passed through the fluid delivery tube 104, the temperature output from the sensor 12 is that reflected by the upper peak 25, which corresponds with the temperature initially calibrated by the sensor 12. The fluid 102, as it is being passed through the fluid delivery tube 104, causes the temperature output by the sensor 12 to drop in accordance with the temperature of the fluid 102 to the point reflected by the lower peak 27. Similarly, the data signal 24 as shown increases upwardly from its lower peak 27 to the upper peak 25 as the flow of the fluid 102 terminates passing through the fluid delivery tube 104. The third signal 26 is illustrative of the steady data signal which corresponds with the output of the sensor 12 when the fluid 102 is either contained within and not moving through the fluid delivery tube 104, or when the fluid delivery tube 104 is in an empty condition.

Figure 3:
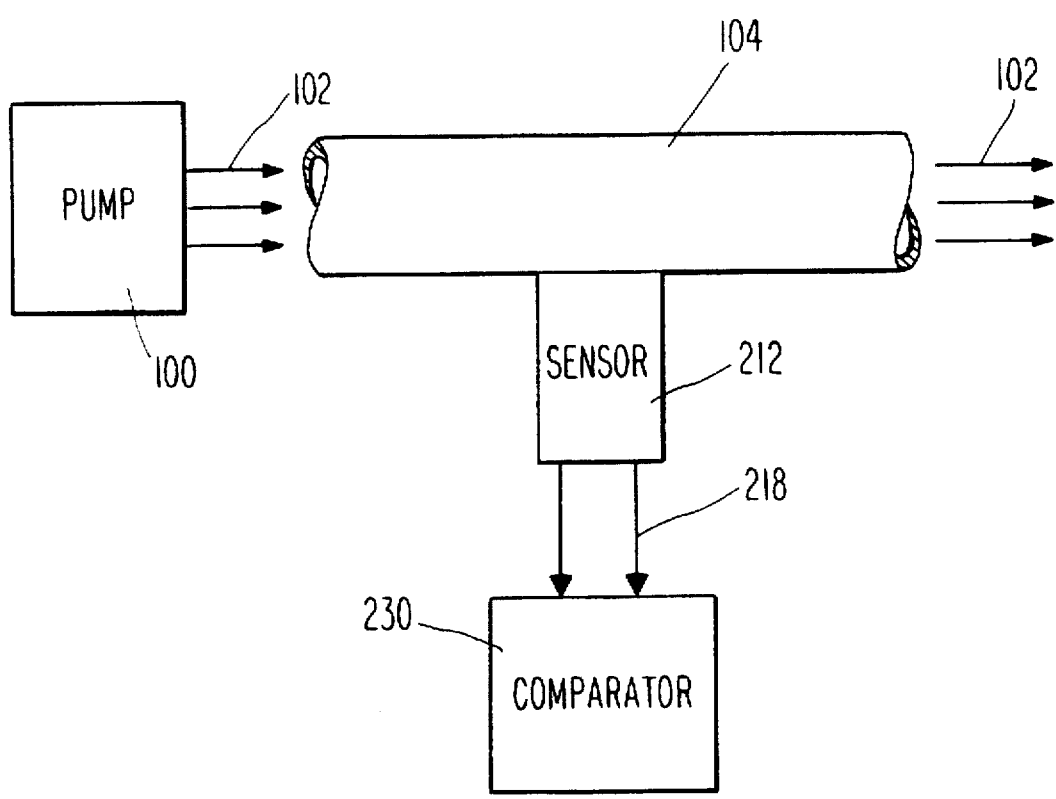
FIG. 3 shows a partly schematic and partly block diagram representation of the non-invasive monitoring system and method in accordance with a second embodiment of the present invention.

An alternate embodiment of the non-invasive monitoring system and method according to the present invention is illustrated in FIG. 3. As is shown in this second embodiment, portions corresponding with the portions disclosed in relation to the first embodiment are identified by the numbers beginning with the number 200. The fluid delivery system as disclosed in this embodiment is identical to that previously described and is numbered accordingly consistent with the first embodiment. The non-invasive monitoring system and method as shown in FIG. 3 includes a sensor 212 corresponding to the sensor 12 of the first embodiment and a comparator 230. The comparator 230 as shown is connected via the lines 218 with the sensor 212. The comparator 230 as disclosed in this embodiment can be comprised of any suitable comparator or similar device commonly known in the art. In operation, the sensor 212 provides the data in the form of analog signals associated with its monitored temperature via the lines 218 to the comparator 230. The comparator 230 receives these analog signals from the sensor 212 and then processes these against previously stored critical threshold values, similar to that disclosed earlier in relation to the microcontroller 16.

As indicated earlier, the non-invasive monitoring system and method of the present invention possesses several advantages over conventional methods and systems. A particular advantage is that the present invention provides a simple interface between the sensor and the fluid delivery tube. In particular, the sensor 12 or 212 is merely placed into contact with the outer surface of the fluid delivery tube 104 in order to monitor the fluid 102 of the system. This provides for a simple and inexpensive procedure since intricate interfacing arrangements between the sensor and the tubing are not required. Another benefit of this simple sensor/tube interface is that the device can have application with many different types of fluid delivery systems. Furthermore, another advantage is that the present invention can incorporate standard electronic elements which further facilitates a less complex and more economical system.

It will be recognized by those skilled in the art that changes may be made by the above-described embodiments of the invention without departing from the broad inventive concepts thereof. For example, the microcontroller 16 or comparator 230 can also be associated with or connected to other devices, for example to provide regulation of the fluid delivery system in accordance with the status of the fluid 102 in the fluid delivery tube 104. For instance, the microcontroller 16 or comparator 230 can be included with a display for indicating to the user of the device the status of the fluid 102 inside the fluid delivery tube 104. In addition, these elements can also be adapted to cease operation of the fluid delivery system corresponding with the status of the fluid 102, such as by terminating operation of the pump 100. Furthermore, the microcontroller 16 or comparator 230 can also be adapted to analyze the temperature data provided from the sensor means against known temperature profiles, for example that associated with a particular fluid delivery system or pump device, such as shown in Fig. 2. It is understood, therefore, that this invention is not limited to the particular embodiments disclosed, but it is intended to cover all modifications which are within the scope and spirit of the invention as defined by the appended claims.

I claim:

1. A non-invasive monitoring system comprising, with a fluid delivery system having a fluid delivery pump delivering fluid having a particular fluid temperature in pulses through a fluid delivery tube:

sensor means which comprises a self-heated temperature sensor calibrated at an initial temperature, with the initial temperature being different from the temperature of the fluid, the sensor means being adapted to engage an outer surface of the fluid delivery tube and thereafter responsive to the fluid when passing through the fluid delivery tube for changing the initial temperature of the sensor means as a result of the fluid temperature when the fluid is being passed through the fluid delivery tube, the sensor means returning to the initial temperature when the fluid is not being passed through the fluid delivery tube, the sensor means also being adapted for generating data corresponding with the initial temperature and the changing of the initial temperature thereof;

means for monitoring the data from the sensor means for detecting the changes in the initial temperature as influenced by the temperature of the fluid when passing through the fluid delivery tube; and means for processing the data from the sensor means corresponding to the initial temperature and the changing of the initial temperature thereof for determining the status of the flow of fluid in the delivery tube, wherein said processing means comprises analyzing means adapted to identify steady data conditions corresponding to a steady temperature patern indicating that either no fluid is moving inside the fluid delivery tube or that the fluid delivery tube is empty and identifying oscillating data conditions corresponding to an oscillating temperature pattern indicating that fluid is being passed in pulses through the fluid delivery tube.

2. A non-invasive monitoring system according to claim 1, wherein the processing means comprises means for analyzing the data from the sensor means associated with the initial temperature and the changes in the initial temperature thereof against known data conditions for determining the status of the flow of the fluid in the fluid delivery tube.

3. A non-invasive monitoring system according to claim 2, further including display means in association with the analyzing means adapted for providing a display of the status of the fluid in the fluid delivery tube.

4. A non-invasive monitoring system according to claim 1, wherein the sensor means generates data in the form of analog signals representative of the initial and changed temperatures thereof for analysis.

5. A non-invasive monitoring system according to claim 4, wherein the monitoring means includes conversion means adapted for placing the data generated by the sensor means in form for analysis, wherein the conversion means comprises:

analog to digital convertor means for converting the analog signals generated by the sensor means to digital signals; and computer means coupled to the analog to digital convertor means adapted for receiving the digital signals therein.

6. A non-invasive monitoring system according to claim 1, wherein the initial temperature of the sensor is elevated above the temperature of the fluid.

7. A non-invasive monitoring system according to claim 1, wherein the self-heated temperature sensor comprises a thermistor.

8. A non-invasive method for monitoring a fluid delivery system of the type including a fluid delivery pump delivering fluid having a particular fluid temperature in pulses through a fluid delivery tube, the non-invasive method comprising the steps of:

providing a sensor means calibrated at an initial temperature and adapted for monitoring a temperature of a source external thereto, the sensor means being responsive to the temperature of the sensor means as a result of the external source temperature when in communication therewith, the sensor means being adapted to return to the initial temperature when not in communication with the external source and generating data corresponding with the initial temperature and the changing of the initial temperature thereof;

calibrating the initial temperature of the sensor means different from the temperature of the fluid;

contacting the sensor means with an outer surface of the fluid delivery tube;

monitoring the data from the sensor means for detecting the changes in the initial temperature thereof as influenced by the temperature of the fluid when passing through the fluid delivery tube; and processing the data from the sensor means corresponding to the initial temperature and the changes in the initial temperature thereof for determining the status of the flow of the fluid in the fluid delivery tube, wherein the processing step involves identifying steady data conditions corresponding to a steady temperature pattern indicating that either no fluid is moving inside the fluid delivery tube or that the fluid delivery tube is empty and identifying oscillating data conditions corresponding to an oscillating temperature pattern indicating that fluid is being passed in pulses through the fluid delivery tube.

9. A non-invasive method for monitoring a fluid delivery system according to claim 8, wherein the step of processing the data from the sensor means associated with the initial and changed temperatures thereof further comprises the step of analyzing the data from the sensor means against known data conditions for determining the status of the fluid in the fluid delivery tube.

10. A non-invasive method for monitoring a fluid delivery system according to claim 9, wherein the step of analyzing the data from the sensor means further includes the step of displaying the status of the fluid in the fluid delivery tube.

11. A non-invasive method for monitoring a fluid delivery system according to claim 8, wherein the sensor means generates data in the form of analog signals representative of the initial and changes in the initial temperatures thereof for analysis.

12. A non-invasive method for monitoring a fluid delivery system according to claim 11, wherein the step of monitoring the sensor means includes the step of converting the analog signals generated by the sensor means to digital signals for analysis.

13. A non-invasive method for monitoring a fluid delivery system according to claim 12, wherein the step of processing the data from the sensor means further includes the step of analyzing the digital signals to determine the status of the flow of the fluid in the fluid delivery tube.

14. A non-invasive method for monitoring a fluid delivery system of the type including a fluid delivery pump delivering fluid having a particular fluid temperature in pulses through a fluid delivery tube, the non-invasive method comprising the steps of;

providing a self-heated temperature sensor in engagement with an outer surface of the fluid delivery tube;

calibrating the self-heated temperature sensor to an initial temperature different from the temperature of the fluid;

monitoring the self-heated temperature sensor for determining the changes in the initial temperature thereof as influenced by the temperature of the fluid when passing through the fluid delivery tube; and processing the changes in the initial temperature of the self-heated temperature sensor for determining the status of the flow of the fluid in the fluid delivery tube, wherein said processing step includes identifying steady data conditions corresponding to a steady temperature pattern indicating that either no fluid is moving inside the fluid delivery tube or that the fluid delivery tube is empty and identifying oscillating data conditions corresponding to an oscillating temperature pattern indicating that fluid is being passed in pulses through the fluid delivery tube.

15. A non-invasive method for monitoring a fluid delivery system according to claim 14, wherein the step of processing the data from the sensor corresponding to the initial and changed temperatures thereof further comprises the step of analyzing the data from the sensor against known data conditions for determining the status of the flow of the fluid in the fluid delivery tube.

16. A non-invasive method for monitoring a fluid delivery system according to claim 15, wherein the step of analyzing the data from the sensor further includes the step of displaying the status of the fluid in the fluid delivery tube.

17. A non-invasive method for monitoring a fluid delivery system according to claim 14, wherein the sensor generates data in the form of analog signals representative of the initial and changed temperatures thereof for analysis.

18. A non-invasive method for monitoring a fluid delivery system according to claim 17, wherein the step of monitoring the sensor includes the step of converting the analog signals generated by the sensor to digital signals for analysis.

19. A non-invasive method for monitoring a fluid delivery system according to claim 18, wherein the step of processing the data from the sensor further includes the step of analyzing the digital signals to determine the status of the fluid in the fluid delivery tube.

20. A non-invasive method for monitoring a fluid delivery system according to claim 14, wherein the initial temperature of the self-heated temperature sensor is elevated to a temperature above the temperature of the fluid.

* * * * *